United States Patent [19]

Crossway et al.

[11] Patent Number: 4,743,548

[45] Date of Patent: May 10, 1988

[54] PLANT CELL MICROINJECTION TECHNIQUE

[75] Inventors: Anne Crossway; Daniel Facciotti, both of Davis, Calif.

[73] Assignee: Calgene, Inc., Davis, Calif.

[21] Appl. No.: 761,735

[22] Filed: Aug. 1, 1985

Related U.S. Application Data

[63] Continuation-in-part of Ser. No. 654,606, Sep. 25, 1984, abandoned.

[51] Int. Cl.⁴ .................... C12N 15/00; C12N 5/02
[52] U.S. Cl. .................... 435/172.3; 435/240.47; 935/53; 935/67
[58] Field of Search .............. 435/172.1, 240, 241, 435/317, 948, 172.3; 47/58; 935/53

[56] References Cited

PUBLICATIONS

A. Crossway (1984) Agricell Report p. 28, Apr.
H. Steinbiss et al. (1983) Protoplasma 116:223–227.
H. Koop et al. (1983) Z. Pflanzenphysiol. Bd. 112:21–34.
I. Potrykus (1979A) Plant Science Letters 14:231–235.
Y. Gleba (1978) Mol. Gen. Genet. 165:257–264.
T. Nagata et al. (1970) Planta (Berl) 92:301–308.
R. Brinster et al. (1981) Cell 27:223–231.
T. Wagner et al. (1981) Proc. Natl. Acad. Sci. U.S.A. 78:6376–6380.
T. Lin (1966) Science 151:333–337.
J. Gordon et al. (1981) Science 214:1244–1246.
Griesbach, 1983, Plant Molecular Biology Reporter 1:32–37.
Hess, D. 1977, Cell Modification by DNA Uptake, pp. 506–535 In: Plant Cell, Tissue, and Organ Culture, Springer-Verlag, New York.
Wullems et al. 1981, Proc. Natl. Acad. Sci. U.S.A. 78(7): 4344–4348.
Reich et al. 1984, J. Cell. Biochem. Suppl. (8 Part B): 60.
Rasmussen et al. 1984, Derwent Biotech. Abstr. #9217, vol. 3, p. 58.
Russell et al. 1983, Derwent Biotech. Abstr. #6980, vol. 2, p. 48.
Tilton et al. 1983, Derwent Biotech. Abstr. #6981, vol. 2, p. 48.
Potrykus et al., 1979B, Theor. Appl. Genet. 54:209–214.
Evans et al. 1983, Protoplastisolation and Culture, pp. 125–176 In Handbook of Plant Cell Culture, vol. 1, Evans, et al., eds. MacMillan Publishing Co., New York.

Primary Examiner—Charles F. Warren
Assistant Examiner—David T. Fox
Attorney, Agent, or Firm—Bertram I. Rowland

[57] ABSTRACT

Microinjection techniques for plant protoplasts utilize a holding pipette for immobilizing the protoplast while an injection pipette is utilized to inject the macromolecule. In order to manipulate the protoplasts without damage, the protoplasts are cultured for from about 1 to 5 days before the injection is performed to allow for partial regeneration of the cell wall. It was found that injection through the partially regenerated cell wall could still be accomplished and particular compartments of the cell could be targeted. The methods are particularly useful for transformation of plant protoplasts with exogenous genes.

8 Claims, 1 Drawing Sheet

PLASMID pCGN561

PLASMID pCGN169

HIII - HindIII      SaI - SmaI      EI - EcoRI
BHI - BamHI         PI  - PstI      BII - BglII
S1I - SalI

PLANT CELL MICROINJECTION TECHNIQUE

This application is a continuation-in-part of application Ser. No. 654,606, filed Sept. 25, 1984, now abandoned, which disclosure is incorporated herein by reference.

BACKGROUND OF THE INVENTION

1. Field of the Invention

The ability to transfer exogenous genetic material into higher plants promises to provide enhanced opportunities for agricultural scientists to increase food production in the coming decades. At present, the primary focus of those interested in the genetic manipulation of higher plants has been in two areas: use of the Ti plasmid of *Agrobacterium tumefaciens* and use of vectors based on the Caulimoviruses. While these systems offer the potential to integrate exogenous DNA into the plant's genome, they each suffer from many drawbacks including plant host range, efficiency of transformation, lengthy manipulative procedures, and the like. It would thus be desirable to have an improved system for the genetic manipulation of plants.

Direct microinjection of DNA as practiced in animal cells has many advantages, including simplicity and very high transformation rates. Despite these advantages, the utilization of direct microinjection of DNA into plant cells has found only limited use. Direct microinjection of plant cells is complicated by the presence of a rigid cell wall not found in animal cells. While protoplasts lacking the cell wall can be formed, the microinjection of plant cell protoplasts is made difficult by their extreme fragility. Successful microinjection has been achieved by immobilizing plant protoplasts on a solid substrate. Such immobilization, however, prevents easy separation of injected and non-injected cells, and the small percentage of injected cells can only be followed for a few days. A strong selectable marker would be required to allow identification and recovery of transformed cells, and the use of such markers may result in the loss of a significant portion of the transformed material.

Thus, it would be desirable to provide a method for the direct microinjection of DNA and other macromolecules into plant protoplasts, which method provides a high rate of uptake of the injected DNA into specified compartments of the plant cell with high viability of the injected protoplasts.

2. Description of the Prior Art

Steinbiss and Stabel (1983) Protoplasma 116:223-227 teach the microinjection of macromolecules into plant protoplasts where the protoplasts are first attached to microscope cover slips using polylysine. Although functional, the attachment with polylysine reduces the protoplast viability and microinjection into the nucleus occurs infrequently. Griesbach (1983) Pl. Mol. Biol. Rep. 4:32-37 discloses the microinjection of chromosomes into higher plant protoplasts that are either free-floating or suspended in agar. Injection into the nucleus was not obtainable and protoplast viability was severely reduced. The microinjection of DNA into mouse eggs using a holding pipette and a microinjection pipette is described in Lin (1966) Science 151:333-337. See also, Wagner et al. (1981) Proc. Natl. Acad. Sci. USA 78:6376-6380; Brinster et al. (1981) Cell 27:223-231; and Gordon and Ruddle (1981) Science 214:1244-1246, where the successful transfer and expression of genetic material into the genomes of newborn mice by microinjection is described. See also, Lawrence and Davies, Plant Cell Reports (1985) 4:33-35, who describe a protoplast microinjection technique.

SUMMARY OF THE INVENTION

An improved method for microinjecting DNA and other macromolecules into plant cells, varying from intact cells to protoplasts, is provided for protoplasts. After removing the cell wall, the protoplasts are precultured for a period of time sufficient to partially regenerate the cell wall. Injection of the DNA or other macromolecule is accomplished using a specially formed injection pipette while the cells are immobilized. In the preferred embodiment, plant cells are held by suction using a holding pipette while the injection pipette is inserted into the cell. Injected cells are collected together and may be cultured in isolation from other cells.

BRIEF DESCRIPTION OF THE DRAWINGS

The present invention will be better understood by reference to the following attached drawings that form a part of the present specification, wherein.

DESCRIPTION OF THE SPECIFIC EMBODIMENTS

Figure 1A:
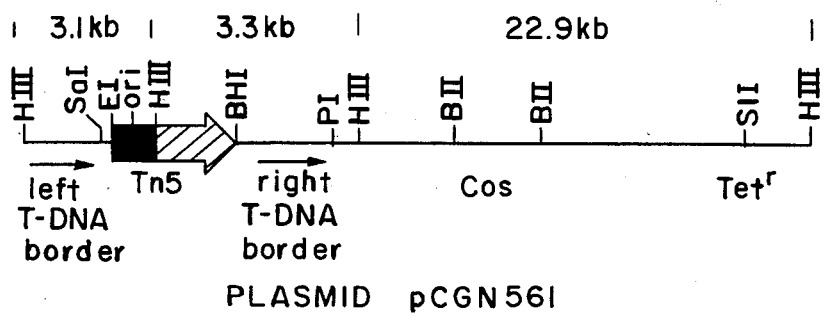
FIG. 1A is a representation of plasmid pCGN561. The HindIII fragment shown was inserted into plasmid RK290.

The present invention provides a novel method for injecting nuclei into plant cells. The nucleic acid may be present in a variety of forms and environments. The nucleic acid DNA or RNA may be a construct of relatively small size, less than 1 cM, usually less than about 100 kbp, a virus, a chromosome or fragment thereof, an organelle, such as a nucleus or plastid, e.g., chloroplast, or a prokaryotic cell, e.g., *Agrobacterium tumefaciens* or *rhizogenes*. The plant cells which are injected can be employed in various forms, with or without cell walls or other natural protective coating, as is found with protoplasts, intact cells, seeds, pollen grains, or multicellular structures.

The procedure for the various nucleic acid sources and the different forms or states of cells will be similar. Therefore, the description of the injection of nucleic acid into protoplasts will be treated as paradigmatic. Where the protocol is different or may vary depending upon the nature of the nucleic acid or cell, the differences will be indicated. Protoplasts will be different from the plant cells which retain their cell wall in that protoplasts require prior treatment of plant cells. For the most part, cells other than protoplasts will not require prior treatment.

For protoplasts, the cell wall is removed in accordance with conventional methods. The plant tissue may be dispersed in an appropriate medium having an appropriate osmotic potential, e.g., 3 to 8 wt. % of a sugar polyol, and one or more polysaccharide hydrolases, e.g., pectinase, cellulase, etc., and the cell wall degradation allowed to proceed for a sufficient time to provide protoplasts. After filtration the protoplasts may be isolated by centrifugation and may then be resuspended for subsequent treatment or use. If desired, the cell wall may only be partially degraded so that the wall retains substantial integrity, but is less resistant to syringe needle puncture.

After preparing the protoplasts, the freshly prepared protoplasts are maintained in a culture for an amount of time sufficient to partially regenerate the cell wall prior to injection of the macromolecules. The partial cell wall provides sufficient mechanical support to preserve the protoplast during the injection, while allowing penetration by the injection means, typically an injection pipette.

The cells, for example, the partially-regenerated protoplasts, are individually manipulated using a holding pipette which is adapted to hold the protoplast by applying a small suction on the partially regenerated cell wall. Using the holding pipette, the user is able to orient the cell or protoplast to expose the nucleus. With pollen grains or multicellular structures such as seeds, a larger holding pipette may be employed or a pair of pipettes, which may be manipulated in the manner of forceps. An injection pipette is then used to penetrate the cell or protoplast and inject the macromolecule directly into the nucleus. The ability to inject directly into the nucleus is important to allow transformation of cells or protoplasts by injection of DNA. The injected cells or protoplasts are then cultured separately, as appropriate, to allow the injected cells and resulting culture to be observed in isolation from non-injected cells.

The large nucleic acid macromolecules, such as chromosomes and organelles, e.g. chloroplasts and nuclei, may be obtained intact in a variety of ways. Protoplasts are a particularly useful source and may be prepared in conventional ways. The chromosomes or organelles may then be isolated and purified, being freed of cellular debris. Methods for obtaining these nucleic acid components are described in de Laat and Blaas, *Theor. Appl. Genet.* (1984) 67:463; Kobza and Edwards, Isolation of Organelles: Chloroplasts, 1984, In: *Cell Cultures and Somatic Cell Genetics of Plants*, Vol. 1, Laboratory Practices and Their Applications (Vasil, ed.) Academic Press, Inc., N.Y.; Zuily-Fodil et al., *Physiol. Plant* (1978) 43:201: Hadlaczky et al., *Planter* (1983) 157:278; and Tulp et al., (1979) A Sorter of Cells, Chromosomes and Nuclei That Combines Simplicity With Good Resolution, pp. 45–50, In: Separation of Cells and Subcellular Elements, Pergamon Press, whose disclosures are incorporated herein by reference.

The method of the present invention is useful with cells from virtually any higher plant. In particular, the method is useful with cells from higher plants which possess totipotency and from which the entire plant can be regenerated.

The subject method can be used with cells from any vegetation. Classes of interest include gymnospermae and angiospermae, the latter includes the subclasses monocotyledoneae and dicotyledoneae. Plants of interest include the grasses (grains), vegetables, fruits, flowering plants, legumes, tubers, and the like.

With protoplasts, current methods exist for protoplast regeneration from various species of *Solanaceae*, such as *Solanum tuberosum* (potato), *Lycopersicum esculentum* (tomato), *Nicotiana tabacum* (tobacco), *Solanum melogena* (eggplant), *Capsicum annuum* (peppers), and various petunias, e.g., *Petunia hybrida*.

In addition to these, other valuable economic crops, such as cereals, wood plants, legumes, and the like, have been regenerated from protoplasts under particular conditions. It is expected that the ability to regenerate whole plants from plant protoplasts will improve as the particular conditions for such regeneration, e.g., plant hormones, protoplast density, pH, light, and the like, are identified.

Of particular interest in the subject invention is the modification of higher plants by transformation of plant cells, particularly protoplasts, and, as appropriate, regeneration of the protoplasts into cells, and growth of the cells into the whole plant using DNA constructs and/or DNA foreign to the plant cell. (Foreign intends that the DNA is not naturally found in the host cell.)

A wide variety of structural genes along with other DNA, as present in individual chromosomes, nuclei or DNA constructs may be introduced into the protoplast to become integrated into the plant genome. The DNA may be "bare" or incorporated into a vector system, e.g., systems based on the Ti plasmid or the Caulimoviruses. The structural genes introduced may provide for a wide variety of modifications. By introducing genes which control various functions, the functions of the plant can be widely varied. Plant growth can be inhibited or enhanced. Nutrient requirements may be modified. Production of various plant products can be increased or decreased. Enhanced protein and/or saccharide content can be provided. The plant can be adapted to survive in hostile environments, such as reduced light, lower temperature, brackish water. Protection against bacterial and pest infection can also be provided. Herbicide resistance may be imparted to the cells. These and other modifications can be achieved by providing structural genes which produce the particular proteins responsible for these characteristics.

Protoplasts may be formed by enzymatically digesting the cell wall of a desired plant cell using a cellulase, typically a fungal cellulase. For example, plant leaves may be macerated, the main veins discarded and the macerate treated with a solution of an osmoticum and the cellulase. The resulting protoplasts may be pelleted and washed to remove the cellular debris. A specific method for forming tobacco mesophylls is set forth in the Experimental section hereinafter. Other methods for forming plant protoplasts are well known in the art.

The freshly prepared protoplasts are cultured in a suitable nutrient medium for an amount of time sufficient to partially regenerate the cell wall to facilitate subsequent manipulation. The partially regenerated cell wall does not inhibit penetration by the injection pipette into the protoplasts. The amount of time required for regeneration will vary depending on the cell type, the culturing conditions, and the like. Injection may be performed prior to complete regeneration of the cell wall (which occurs immediately prior to first cell division). Typically, the regeneration time will be at least one day and will not exceed five days. More typically, regeneration time will be between one and three days. It may be desirable, although not necessary, to determine the extent of cell wall regeneration by the method of Nagata and Takebe, Planta (Berl) (1970) 92:301–308. Using this method, the time required for cell wall regeneration under the particular conditions may be determined. Microinjection may then be timed to occur when the cell walls have substantially regenerated in a majority of the protoplasts, but before first cell division.

Prior to protoplast injection, it is necessary to immobilize the cell so that the injection pipette can be inserted through the partially-regenerated cell wall. A holding pipette (as described below) is utilized to grasp an individual protoplast from the culture and to manipulate the protoplast during injection. Injection is accomplished under aseptic conditions using an ultrafine injection pipette. Conveniently, to maintain aseptic conditions, a drop of the protoplast suspension and a drop of the nucleic acid solution, e.g., DNA solution, are formed adjacent one another and covered with oil. In the exemplary embodiment, this is accomplished using a microscope slide having a depression to contain the suspension and solution under the oil. The holding pipette and injection pipette are then manipulated using commercially available manipulators while viewing under the microscope. The protoplasts will be oriented to expose the nucleus to allow direct injection of the DNA into the nucleus.

The holding pipette may be prepared from commercially available capillary tubing, typically 1.0 millimeter tubing, using a pipette puller in the conventional manner. The holding pipette is first pulled to form a tapered end, and the taper is broken at a particular orifice diameter depending on the size of the protoplasts. The tip is broken by annealing, typically using a heated glass bead, followed by rapid cooling. The broken surface is then fire-polished by holding it close to the heated filament. The orifice diameter of the pipette should be equal to about one quarter the diameter of the cell. Thus, for a typical tobacco cell protoplast having a diameter of about 40 microns, the orifice of the holding pipette should be about 10 microns. The remote end of the pipette may be bent to facilitate observation during manipulations within the depression slide. With other than protoplasts, the diameter of the orifice may be up to 0.5× the diameter of the cell or more, being less than the diameter of the cell. In some instances a flexible tip, e.g. silicone, may be employed, particularly with large cellular targets.

The injection pipette is also formed by pulling a standard glass capillary tube on a commercially available pipette puller. The tube is pulled until it breaks at its narrowest point, leaving an extremely fine tapered tip. The tip of the pipette is on the order of one micron in diameter. The injection pipette may be calibrated by measuring the length and basal diameter of the portion of the pipette tip which will hold the injection solution. Estimation of the volume injected is then made by observing the shift in the meniscus between the nucleic acid solution and the oil and applying the appropriate geometric formula. To facilitate introduction of larger structures, such as chromosomes, nuclei, and other organelles, the tip of the injection pipette may be internally beveled to increase the internal orifice diameter without increasing the outside diameter.

The holding and injection pipettes are filled with a viscous oil, typically paraffin oil, and inserted into suitable micromanipulators. The remote ends of the pipettes are connected to syringes by plastic tubing also filled with oil. Thus, the pressure within the pipette can be manipulated by adjusting the syringes. The depression slide holding the DNA and protoplast solution is placed underneath the viewing microscope and both the holding pipette and injection pipette are brought into focus. Before immersing the tips of the pipettes beneath the oil layer, the tip of the injection pipette is removed by touching it against the holding pipette, leaving an opening of about one micron.

The injection pipette is next inserted into the nucleic acid solution drop, and approximately 10 pL of the solution is drawn in using the associated syringe. The injection pipette is then removed from the drop, and both the injection pipette and the holding pipette are lowered into the protoplast solution. Protoplasts are grasped individually by holding the orifice of the holding pipette adjacent the protoplast and applying a small suction using the associated syringe. After raising the protoplast, the orientation of the protoplast may be adjusted by gently turning using the injection pipette. Once the nucleus is exposed, the injection pipette may be inserted into the nucleus, and a desired volume of DNA solution, typically 1 to 2 pL, injected.

In some instances instead of injecting into the nucleus compartment, the nucleic acid will be injected into the cytoplasm compartment. This will be feasible where the nucleic acid is capable of migrating from the cytoplasm into the appropriate organelle compartment for integration and replication.

Following injection of the nucleic acid, the protoplasts are regenerated into callus tissue by culturing in an aseptic environment on a phytohormone-containing culture medium. Calli are forced to regenerate into plantlets by stimulation with a hormone, e.g., cytokinin, for a short period of time, e.g., one to three days. The genetically-modified plantlets may then be potted in a sterile potting mix and permitted to grow.

The presence of the desired gene in the plant cells can then be established in a wide variety of ways, depending on the nature of the gene. The presence of a gene which produces an exogenous product may be detected by isolation and lysis of the plant cell and an analysis of the cytoplasm for the exogenous product, or of the nucleus for the exogenous gene. The exogenous product may be detected by electrophoresis, chromatography, immunoassay, or the like. The gene can be detected conveniently by hybridization, for example, by using Southern Blotting.

Once a plantlet or plant has been shown to have been transformed, the cells of the plant may then be used repeatedly for tissue culture, followed by the growth of plantlets. Thus, the modified plant can be repetitively regenerated by use of cell and tissue culture. In some instances, propagation may be maintained from seed, although monitoring for loss of the exogenous gene would be advisable.

To facilitate identification of transformed protoplasts, it is desirable that the injected protoplasts be cultured in isolation from non-injected protoplasts. To do so, however, requires microculture techniques since plant protoplasts typically require a minimum density of $10^4$ to $10^6$ cells per milliliter. By employing very small culture volumes, the density of injected cells can be kept within the requisite range without requiring a very large number of transformed protoplasts.

A particular technique for the microculture of protoplasts is accomplished by forming a hanging drop of culture solution on a plate inverted over a suitable solution. The drop will usually be not greater than about 0.3 $\mu L$, usually less than about 0.25 $\mu L$, having from about 10–50, usually 20 to 40 protoplasts. Conveniently, a petri dish lid can be used and inverted over a petri dish including an aqueous medium, e.g. a culture medium. The enclosed system is maintained at the proper temperature, and the resulting humidity inhibits the evaporation of media from the hanging drops. Particularly, the osmolality of the medium at the bottom of the dish should be less than the hanging drop. Conveniently about 40% of the osmolality of the drop, so as to maintain nondehydrating conditions for the drop.

Growth of the hanging drop cultures may be monitored under a microscope, and medium added as the microcalli grow. Media is replenished or changed using a small pipette.

A conventional medium may be employed, e.g., Murashige-Skoog (MS) medium having appropriate amounts of plant hormones, auxins, e.g., 0.1–0.25 mg/L of 2,4-dichlorophenoxyacetic acid and 0.5–0.75 mg/L of naphthaleneacetic acid, and cytokinins, e.g., 0.6–1 g/L of kinetin. The initial medium concentration will be about 0.3–0.5 M conditioned MS medium, with successively reduced molality to about 0.15–0.25 M. The period of time for growth in the hanging drop will be from about 3–5 weeks. After this time the expanded microcalli containing drop may be transferred to a surface, e.g., petri dish, as a lying drop and the medium maintained and replenished at the low range of molality indicated above. Individual calli may then be transferred to solid medium, MS plus 0.5% agarose.

For other than protoplasts, those cells which may be grown in culture such as cultured cells, microspores, clumps of callus, or the like, may be grown as described above. For other cellular assemblies, such as seed and pollen grains, these would be directly fertilized and germinated.

When the calli reach a sufficient size, typically about 1.0 mm in diameter, they may be transferred to agar plates containing a suitable medium. Plantlets may be regenerated from the microcalli using conventional techniques, as described above.

The following examples are offered by way of illustration, not by way of limitation. The following abbreviations are used:

BAP—Benzylaminopurine
IAA—Indole acetic acid
NAA—Naphthalene acetic acid

EXPERIMENTAL

Materials and Methods

1. Preparation of Tobacco Mesophyll Protoplasts

Protoplast donor plants of *Nicotiana tabacum* cv. xanthinc were grown in glass jars under aseptic conditions as described by Facciotti and Pilet (1979) Pl. Sci. Lett. 15:1–6. Apical shoots were placed into 100 ml of agar medium (0.6% Gibco Phytagar MS medium containing 30.0 g/l sucrose, 1.0 mg/l IAA and 0.15mg/l kinetin, pH adjusted to 5.75 prior to autoclaving). The cultures were kept at 23°±2° C. under a 12 hour dark/light regime. Young leaves were removed from 2–3 week old plants, the main veins discarded, and the leaf blades infiltrated in a 6% sorbitol solution with 0.04% pectinase (Pectolyase Y-23) and 0.4% cellulase (Onozuka RS). After 2–3 hours incubation, the macerate was passed through a 149μ nylon filter. The protoplasts were pelleted by centrifugation at 50 xg and washed twice with 6% sorbitol solution. The protoplasts were then suspended at a density of $1-2\times10^5$/ml in modified MS medium (0.5 MS concentration, Gibco 510-1118, plus 5.0 g/l sucrose, 71.0 g/l sorbitol) with 3.0 mg/l NAA and 1.0 mg/l BAP as described by Caboche (1980) Planta 194:7–18.

Preculturing prior to injection was performed in 9.0 cm Parafilm-sealed petri dishes at 23°±2° C. in the dark for 2–5 days.

2. Slide Preparation

All procedures were performed in a laminar flow hood. Depression slides were made by gluing a coverslip over a square hole cut into a plexiglass slide. When inverted, a depression was formed in which all manipulations were performed.

Protoplasts were selected under a dissecting microscope from the cultures prepared, as described above. Selection and transfer of protoplasts were performed with a glass transfer pipette connected by plastic tubing to a micrometer syringe. Transfer pipettes were pulled by hand over a bunsen burner from 1.2 mm O.D. glass tubing, resulting in an orifice of about 100 to 150μ.

A drop of medium containing the selected protoplasts was formed in the depression on the slide. A second drop comprising the DNA solution to be injected was also formed in the depression. A variety of DNA constructs were injected into an aqueous solution. The depression was then filled with paraffin oil covering both the protoplast and DNA solutions to prevent evaporation and contamination during the subsequent manipulations. Slides used for mock injection and controls (noninjected) were prepared in the same manner, omitting the DNA drop.

3. Pipette Preparation

Injection and holding pipettes were prepared from capillary tubing (Drummond Sci. Co. R6 glass 1.0 mm dia., and Leitz 1.0 mm dia., respectively) which had been previously siliconized (Sigmacote, Sigma Chemical Co.). The capillary tubes were pulled on a pipette puller (Ultrafine, Frederick Haer and Co.) to form tapered ends.

The tapered tip of the holding pipette was broken off at a diameter of 20 to 30μ by annealing it to a heated glass bead attached to the filament of the microforge, followed by rapid cooling. The broken surface was fire-polished by holding it close to the heated filament. A bend of approximately 150° was formed by holding it close to a heated filament on a microforge (DeFonbrune MF-80). The bend facilitates control over the pipette by bringing a greater length of the tip into the focal plane of the microscope.

The injection pipette was similarly bent, but the injection tip was not broken off until later in the procedure.

4. Microinjection Procedure

Microinjections were performed under a Leitz Diavert microscope with Leitz micromanipulators. Holding and injection pipettes were inserted into instrument collars connected to Hamilton syringes by plastic tubing filled with paraffin oil. The two pipettes were brought into cofocus and the tip of the injection pipette was removed by touching it against the holding pipette, leaving an opening of $\leq 1.0\mu$.

The injection pipette was lowered into the DNA drop and approximately 10 pL of the DNA solution was drawn into the pipette. The volume was estimated as described below. The injection pipette was then raised out of the DNA drop and both pipettes were lowered into the protoplast medium drop. Protoplasts were picked up individually by suction on the holding pipette and turned by nudging with the injection pipette until the nucleus was readily accessible. The injection pipette was inserted into the nucleus, and approximately 1–2 pL of DNA solution was injected.

Injection pipettes were calibrated by measuring the length and basal diameter of the portion of the pipette tip holding the injection solution using an eyepiece micrometer. The volume was assumed to be that of a cone. Estimation of the quantity injected was made by observing the meniscus between the DNA solution and oil.

Following microinjection, the injection pipette was removed, and the protoplast was placed at the bottom of the medium drop by reversing suction on the holding pipette.

Mock injections were performed as above except that no fluid was injected from the injection pipette. After all protoplasts were injected, the pipettes were raised out of the depression, and the slide was transferred to the laminar flow hood.

5. Hanging Drop Culture

Under a dissecting scope in the laminar flow hood, the injected protoplasts were picked up with the transfer pipette, excluding as much medium as possible. They were then deposited on the lid of a petri dish, forming a hanging drop when the lid was inverted over the original protoplast culture. The size of the hanging drop was dependent on the number of protoplasts as the flow of medium from the transfer pipette was terminated when the last protoplast was deposited. Control hanging drops were made for each experiment in the same manner using approximately the same number of noninjected protoplasts from depression slides. The hanging drop cultures were then incubated at 23°±2° C. in the dark.

Growth of the hanging drop cultures was monitored by observation of the drops under a dissecting microscope. As microcalli grew, medium was added to replenish nutrient supplies or changed completely to reduce the osmolarity, using a transfer pipette. For the first 1-2 weeks of culture, the microcalli were maintained in the medium in which they were precultured. Additional medium was added occasionally if the microcalli were growing rapidly. After 1-2 weeks, the medium was replaced with the same medium containing only 0.2 mg/l NAA. Every 1-2 weeks, the medium was replaced with this medium except of lower osmolarity (56 g/l sorbitol followed by 20 g/l sorbitol). When the calli reached about 1.0 mm diameter (usually after 1.5-2 months of culture), they were transferred to agar plates containing the same medium (0.6% Gibco Phytagar).

An alternative procedure was also employed. Injected protoplasts are placed in a hanging drop as described above. MS (Gibco 510-1118) medium plus 0.2 mg/l 2, 4-D, 0.8 mg/l KIN, and 0.6 mg/l NAA is used for culturing. Depending on the rate of growth of the microcalli, several additions of 0.4 M conditioned MS medium are made during the first 1-2 weeks of culture followed by additions of 0.3 M conditioned MS medium in the second to third weeks. Conditioned medium is prepared by dilution of MS medium taken from 3-5 day old protoplast cultures with 0.2 M MS medium to obtain conditioned medium with a final osmolarity of 0.4 or 0.3 as desired. Usually around week four, 0.2 M MS medium is added to the hanging drop before moving it to a small (200-500 μl) lying drop prior to addition of 0.2 M MS medium as the calli grow. Individual calli are transferred to solid medium, MS plus 0.5% Seaplaque agarose (FMC Corp., Rockland, Maine), when they reach approximately 1-2 mm diameter.

RESULTS

Freshly isolated tobacco mesophyll protoplasts are fragile and difficult to handle with the holding pipette technique. However, it was found that partial regeneration of the cell wall by preculture of the protoplasts for a period of from 2 to 5 days, greatly improves their resilience and ability to survive microinjection. Selection of protoplasts during slide preparation results in a uniform population of cells with respect to wall regeneration and position of nucleus.

Comparison of protoplast viabilities in mock and DNA injection experiments should indicate whether injection of a DNA solution reduces protoplast viability over and above that caused by physical penetration of the injection pipette.

Viability of injected cells after three days was generally 80-90% of that of noninjected controls. Mock-injected cells averaged 82.0% (Table 1) viability whereas DNA-injected cells averaged 89.9% viability (Table 2) when compared to noninjected cells. Comparison of mean viabilities in injected and control cells (Tables 1 and 2) shows that there is a reduction in viability caused by the penetration of the cells by the injection pipette. However, the magnitude of this reduction is only 10-20%. The mean viabilities in mock injection (Table 1) and DNA injection (Table 2) experiments are very similar. This indicates that injection of picoliter quantities of an aqueous DNA solution does not further reduce viability.

Generally, 15-25 cells can be injected per hour depending on the condition of the protoplasts. This is easily doubled if injection into the nucleus is not required.

For successful culture of the protoplasts in hanging drops, maintenance of cell densities like that of normal protoplast cultures $10^4$-$10^6$ cells per ml) is desirable. Formation of hanging drops of appropriate densities was ascertained by observation with a dissecting microscope. Culture of 10-200 cells in 0.25-20 μl hanging drops resulted in microcalli. When cultured in hanging drops, microinjected protoplasts divided to form microcalli in the same manner as the noninjected protoplasts of the controls.

TABLE 1

Viability of Mock-Injected Tobacco Mesophyll Protoplasts in Hanging Drops Three Days After Injection
Viability
(Viable Cells/Total Cells)

| Experiment | Mock Injected | Control | Viability as % of Control |
|---|---|---|---|
| 1 | 47% (42/90) | 74% (50/67)++ | 64 |
| 2 | 78% (47/60) | 78% (37/48)+ | 100 |
| Mean ± S.D. | 62.5 ± 21.9 | 75.2 ± 9.9 | 82.0 ± 25.5 |

+ and ++ denote average viabilities of 2 and 3 replicates, respectively.

TABLE 2

Viability of DNA-Injected Tobacco Mesophyll Protoplasts In Hanging Drops Three Days After DNA Injection
Viability
(Viable Cells/Total Cells)

| Experiment | DNA Injected | Control | Viability as % of Control |
|---|---|---|---|
| 1 | 53 (16/30) | 73 (22/30) | 73 |
| 2 | 60 (6/10) | 75 (9/12) | 80 |
| 3 | 30 (15/50) | 33 (25/75) | 91 |
| 4 | 82 (45/55) | 50 (40/80) | 164 |
| 5 | 73 (40/55) | 83 (50/60) | 88 |
| 6 | 40 (30/75) | 65 (41/63)+ | 62 |
| 7 | 79 (42/53) | 82 (52/64)+ | 96 |
| 8 | 44 (35/79) | 57 (45/80)+ | 77 |
| 9 | 66 (45/68) | 71 (50/70) | 93 |
| 10 | 54 (25/46) | 72 (43/60)++ | 75 |
| 11 | 45 (25/55) | 45 (25/55) | 100 |
| 12 | 61 (48/79) | 85 (62/73)+ | 72 |
| 13 | 85 (60/71) | 79 (56/71) | 108 |

TABLE 2-continued

Viability of DNA-Injected Tobacco Mesophyll Protoplasts
In Hanging Drops Three Days After DNA Injection
Viability
(Viable Cells/Total Cells)

| Experiment | DNA Injected | Control | Viability as % of Control |
|---|---|---|---|
| 14 | 75 (135/180) | 80 (160/199) | 94 |
| 15 | 78 (80/120) | 85 (85/100) | 92 |
| 16 | 65 (47/72) | 83 (61/74)++ | 78 |
| 17 | 80 (51/64) | 70 (42/60) | 114 |
| 18 | 82 (80/90) | 88 (90/102) | 93 |
| 19 | 70 (75/107) | 86 (105/123)+ | 81 |
| 20 | 71 (50/70) | 92 (66/72)++ | 77 |
| 21 | 53 (45/85) | 67 (55/80) | 79 |
| Mean ± S.D. | 64.1 ± 15.7 | 75.0 ± 15.7 | 89.9 ± 21.2 |

+ and ++ denote average viabilities of 2 and 3 replicates, respectively.

The results of culturing injected cells reported here (see Tables 1 and 2) indicate that introduction of the injection pipette into a tobacco protoplast does lower viability. However, injection of picoliter quantities of an aqueous DNA solution does not further reduce viability. A reduction in viability of only 10–20% does not appear to seriously limit the usefulness of microinjection techniques for plants.

Following the above procedure corn pollen grains were mock injected. The pipette was larger (90 μm i.d.) and had a flexible silicone tip. The pipette was introduced into the pollen through the grain pore. In three experiments germination was achieved in from 10 to 25% of the grains mock injected. (Total no. of grains/total germinated: (1) 4/1; (2) 10/1; (3) 10/1). Thus, germination can be achieved after manipulation with a pipette.

Genomic DNA integration was established in the next study. Following the procedure described above plasmids were injected into the nucleus or cytoplasm of tobacco mesophyll protoplasts. Plasmid pCGN561 (29.3 kb) was injected in about 1–2pL at about $10^3$ copies/pL (picoliter). Plasmid pCGN561 has a HindIII fragment construct inserted into RK290. See FIG. 1A following restriction pattern and functional sequences.

Figure 1B:
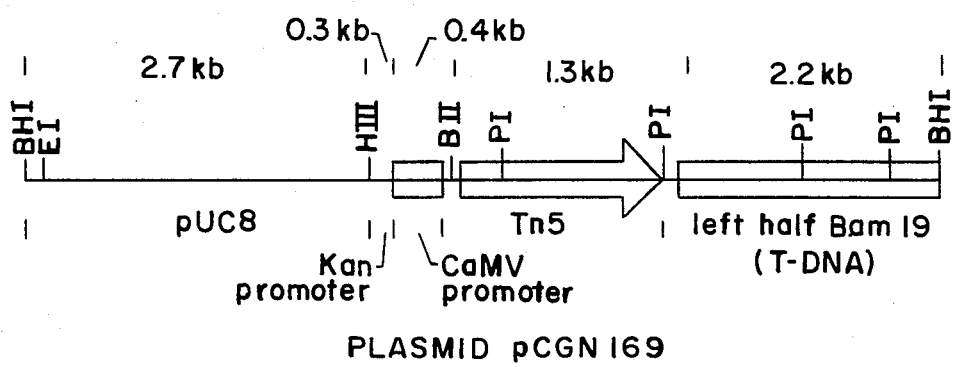
FIG. 1B is a representation of plasmid pCGN169. The Bam HI fragment shown was inserted into plasmid pUC19.

Plasmid pCGN169 (6.9 kb) was injected in about 2 pL at about $10^2$–$10^5$ copies/pL. Plasmid pCGN169 has a BamHI construct fragment inserted into pUC19. See FIG. 1B.

The injection protoplasts were then grown to microcalli and the calli screened by the Southern technique for the presence of the inserted DNA fragments.

pCGN561 Intranuclear Microinjection

| Exp. No. | No. Injected Protoplasts | No. Alive Day 3 | No. Calli Produced | No. Calli Containing 561 DNA |
|---|---|---|---|---|
| 1 | 14 | 11 | 2 | 1 |
| 2 | 21 | 19 | 1 | 0 |
| 3 | 25 | 24 | 24 | 3 |
| 4 | 20 | 15 | 15 | 2 |
| 5 | 33 | 28 | 14 | 2 |
| Total | 113 | 96 | 56 | 8 | pCGN561 Cytoplasmic Microinjection

| Exp. No. | No. Injected Protoplasts | No. Alive Day 3 | No. Calli Produced | No. Calli Containing 561 DNA |
|---|---|---|---|---|
| 1 | 26 | 10 | 1 | 0 |
| 2 | 31 | 22 | 13 | 1 |
| 3 | 43 | 20 | 7 | 1 |
| 4 | 33 | 21 | 5 | 1 |
| 5 | 38 | 14 | 5 | 0 |
| 6 | 32 | 18 | 3 | 0 |
| 7 | 31 | 15 | 2 | 0 |
| 8 | 40 | 28 | 13 | 0 |
| 9 | 30 | 16 | 4 | 0 |
| Total | 304 | 164 | 53 | 3 |

Summary of Southern Analysis Of Transformed Calli from pCGN561 Microinjection

| Type of Injection | Exp. No. | Transformed Callus No. | Approximate Band Sizes (kb) 561 probe | Approximate Band Sizes (kb) kan probe | Approximate No. Copies Per Genome |
|---|---|---|---|---|---|
| Nuclear | 1 | 1 | 11.5 | — | ~1 |
|  |  |  | 10.0 | — |  |
|  |  |  | 3.6 | 3.6 |  |
|  | 3 | 1 | 23.0 | — | 1.2 |
|  |  |  | 3.5 | 3.5 |  |
|  |  | 2 | 3.6 | 3.6 | 0.25 |
|  |  | 3 | 5.4 | — | 0.4 |
|  |  |  | 1.6 | — |  |
|  | 4 | 1 | 5.2 | — | 0.1 |
|  |  | 2 | 4.9 | — | 0.25 |
|  | 5 | 1 | 2.8 | — | 1.2 |
|  |  | 2 | 2.6 | — | 1.2 |
| Cytoplasmic | 1 | 1 | — | 4.5 | ~1 |
|  | 2 | 1 | 3.2 | — | 0.8 |
|  |  |  | 2.5 | — |  |
|  |  |  | 1.4 | — |  |
|  | 3 | 1 | 3.8 | — | ~1 |

According to the present invention, novel methods are provided for the microinjection of macromolecules, chromosomes, nuclei, organelles, and the like into the cytoplasm and nucleus of plant protoplasts. By culturing the protoplasts for a sufficient amount of time to partially regenerate their cell walls, the protoplasts may be manipulated without causing rupture of the fragile protoplast envelope. It has been found that microinjection may be delayed until the cell wall has substantially regenerated, but should be accomplished prior to the first cell division. Microinjection using these techniques provides greatly enhanced viability of the injected protoplasts.

Although the foregoing invention has been described in some detail by way of illustration and example for purposes of clarity of understanding, it will be appreciated that modifications and changes may be practiced within the scope of the appended claims.

What is claimed is:

1. A method for genetically modifying a plant cell capable of proliferation, said method comprising:
   preculturing a protoplast of said cell in a nutrient medium for a time sufficient to regenerate sufficient cell wall to provide a stabilzed protoplast;
   while holding said stabilized protoplast by means of a holding pipette, injecting nucleic acid by means of a micropipette through the membrane of said stabilized protoplast into the cytoplasm or an organelle of said stabilized protoplast, wherein said nucleic acid is capable of replication in a plant cell; and growing said injected protoplast in a nutrient medium, whereby said nucleic acid is replicated and microcalli are formed.

2. A method according to claim 1, wherein said nucleic acid is integrated into a chromosome of said plant cell.

3. A method for genetically modifying a plant cell capable of proliferation, wherein said plant cell is a protoplast, said method comprising:
preculturing said protoplast in a nutrient medium for a time sufficient to partially regenerate the plant cell wall to provide a stabilized protoplast;
while holding said stabilized protoplast by means of a holding pipette, injecting nucleic acid by means of a micropipette through the membrane of said stabilized protoplast, into the nucleus of said protoplast, wherein said nucleic acid is capable of replication in a plant cell;
growing said injected protoplast as a hanging drop in a nutrient medium under non-dehydrating conditions, whereby said nucleic acid is integrated into a chromosome of said plant cell and replicated and microcalli are formed; and
isolating said microcalli.

4. A method for genetically modifying a plant cell capable of proliferation, wherein said cell is a protoplast, said method comprising:
preculturing said protoplast in a nutrient medium for a time sufficient to partially regenerate the plant cell wall to provide a stabilized protoplast;
while holding said stabilized protoplast by means of a holding pipette, injecting nucleic acid by means of a micropipette through the membrane of said stabilized protoplast into the nucleus of said stabilized protoplast, wherein said nucleic acid is capable of replication in a plant cell;
growing said injected protoplast as a hanging drop in a nutrient medium under non-dehydrating condition, wherein the osmolarity of said nutrient medium in the hanging drop is reduced during the proliferation of said cells, whereby said nucleic acid is integrated into a chromosome of said plant cell and replicated and microcalli are formed; and
isolating said microcalli.

5. A method according to claim 13, including the additional step of transferring said microcalli to a lying drop.

6. A method for genetically modifying a plant cell capable of proliferation, wherein said plant cell is a pollen grain, said method comprising:
while holding said pollen grain by means of a holding pipette, injecting nucleic acid capable of replication in a plant cell by means of a micropipette through a grain pore of said pollen grain into the cytoplasm or an organelle of said pollen grain;
fertilizing said pollen gain;
germianting said fertilized pollen grain; and
growing said injected pollen grain in a nutrient medium whereby said nucleic acid is replicated.

7. A method for genetically modifying a plant cell capable of proliferation, said method comprising:
injecting macromolecular DNA into a single protoplast, by holding said protoplast by suction at an orifice of a holding pipette and inserting the tip of an injection pipette carrying said macromolecular DNA into the protoplast and discharging the macromolecular DNA contents of said pipette into the nucleus of said protoplast, wherein said protoplast has been precultured in a nutrient medium for a time sufficient to regenerate sufficient cell wall to provide stability during said injecting; and
growing said injected protoplast in a culture medium of a volume of less than about 0.5 microliters, wherein said medium contains at least about 10 protoplasts, for a sufficient time to produce microcalli.

8. A method according to claim 5, wherein said microcalli regenerate into plantlets by stimulation with a hormone.

* * * * *

UNITED STATES PATENT AND TRADEMARK OFFICE
CERTIFICATE OF CORRECTION

PATENT NO. : 4,743,548
DATED : May 10, 1988
INVENTOR(S) : Anne Crossway and Daniel Facciotti It is certified that error appears in the above-identified patent and that said Letters Patent is hereby corrected as shown below:

Column 14, delete line 16.

Column 14, line 17, delete "fertilized".

Column 14, line 17, replace "germianting" with --germinating--.

Signed and Sealed this

Third Day of April, 1990

Attest:

HARRY F. MANBECK, JR.

*Attesting Officer*      *Commissioner of Patents and Trademarks*